US00PP32621P2

(12) United States Plant Patent
Bergman

(10) Patent No.: US PP32,621 P2
(45) Date of Patent: Dec. 15, 2020

(54) ***LANTANA* PLANT NAMED 'LANZ0019'**

(50) Latin Name: ***Lantana camara* L.**
Varietal Denomination: LANZ0019

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/501,564

(22) Filed: Apr. 30, 2019

(51) Int. Cl.
*A01H 5/02* (2018.01)
*A01H 6/86* (2018.01)

(52) U.S. Cl.
USPC ..... Plt./227

(58) Field of Classification Search
USPC ..... Plt./227
CPC ..... A01H 5/02; A01H 5/00; A01H 6/86
See application file for complete search history.

(56) References Cited

U.S. PATENT DOCUMENTS

PP28,174 P2 * 7/2017 Pan ..... A01H 5/02 Plt./227
PP31,014 P2 * 11/2019 Bergman ..... A01H 5/02 Plt./227
PP31,015 P2 * 11/2019 Bergman ..... A01H 5/02 Plt./227

OTHER PUBLICATIONS

Issuu Syngenta Flowers Annuals & Perennials 2020, retrieved on Jan. 9, 2020, retrieved from Internet at https://issuu.com/floriproservices/docs/a_p_2020_150dpi_uk, cover page and p. 231. (Year: 2019).*
Syngenta Novelty Presentation E2 varieties 2018-2019 Annual Cuttings retrieved on Jan. 9, 2020, retrieved from Internet at https://www.seedstar.sk/assets/img/FPS-varieties-annual-cuttings-season-2018-2019.pdf, pp. 1-2 and 85. (Year: 2019).*

* cited by examiner

*Primary Examiner* — June Hwu
(74) *Attorney, Agent, or Firm* — Dale Skalla

(57) ABSTRACT

A new *Lantana* plant named 'LANZ0019' having medium-large sized dark orange mature flowers, excellent flower production, moderately large plant size and uniform dense mounded habit with medium green foliage.

1 Drawing Sheet

Latin name of the genus and species of the plant claimed: *Lantana camara* L.
Varietal denomination: 'LANZ0019'.

BACKGROUND OF THE NEW PLANT

The present invention comprises a new *Lantana*, botanically known as *Lantana camara* L., and hereinafter referred to by the variety name 'LANZ0019'.

'LANZ0019' is a product of a planned breeding program. The new cultivar 'LANZ0019' has medium-large sized dark orange mature flowers, excellent flower production, moderately large plant size and uniform dense mounded habit with medium green foliage.

'LANZ0019' originated as a natural whole plant mutation discovered among flowering plants of '444-3' growing in a greenhouse in Gilroy, Calif. in November 2014. The parent is the proprietary plant designated as '444-3', dark pink mature inflorescences, while it's similar to 'LANZ0019' in all other characteristics.

The first act of asexual reproduction of 'LANZ0019' was accomplished when vegetative stem cuttings were propagated from the initial selection in December 2014 in a greenhouse in Gilroy, Calif.

BRIEF SUMMARY OF INVENTION

Horticultural examination of plants grown from cuttings of the plant initiated in December 2014 in Gilroy, Calif., and continuing thereafter, has demonstrated that the combination of characteristics as herein disclosed for 'LANZ0019' are firmly fixed and are retained through successive generations of asexual reproduction.

'LANZ0019' has not been observed under all possible environmental conditions. The phenotype may vary significantly with variations in environment such as temperature, light intensity, and day length.

A Plant Breeder's Right for this cultivar has not yet been applied for. 'LANZ0019' has not been made publicly available prior to the effective filing date of this application, notwithstanding any disclosure that may have been made less than one year prior to the effective filing date of this application by the inventor or another who obtained 'LANZ0019' directly from the inventor.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawings show typical flower and foliage characteristics of 'LANZ0019' with colors being as true as possible with an illustration of this type.

Figure 1:
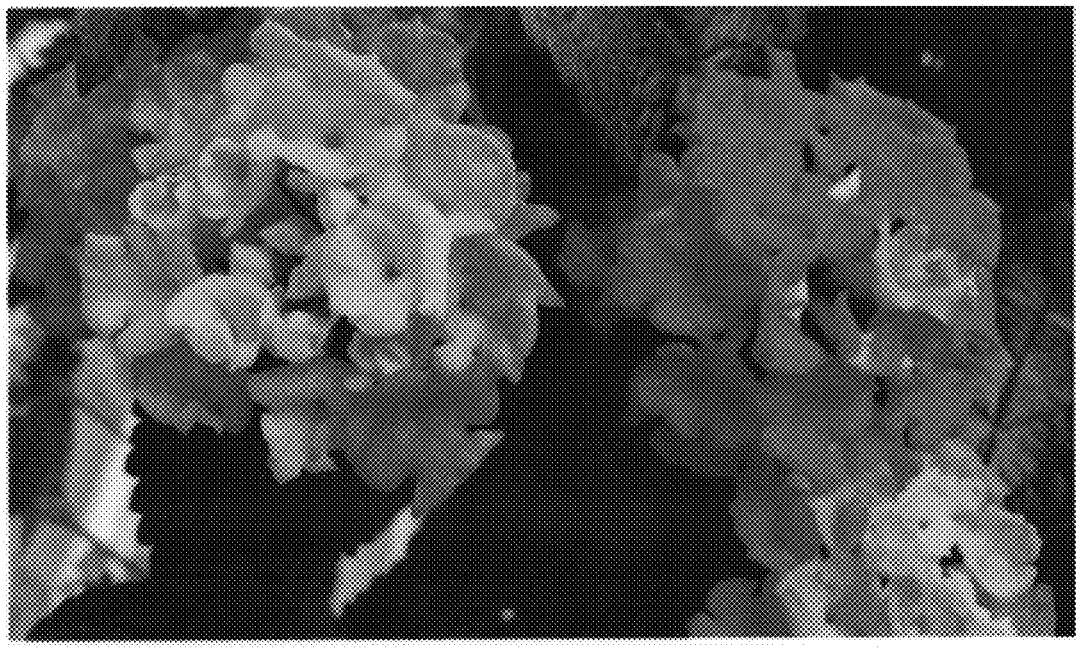
Figure 2:
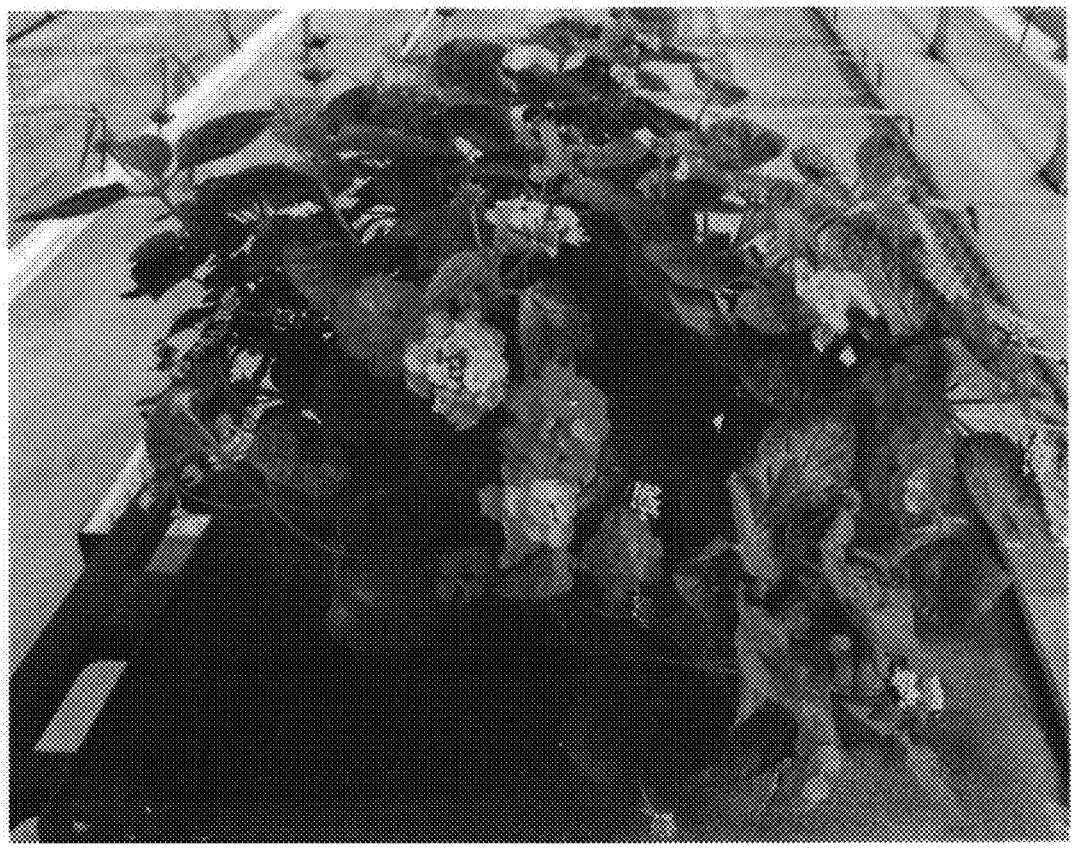

The photographic drawings show in FIG. 1 a close view of an inflorescence, and in FIG. 2 a whole flowering plant.

DETAILED BOTANICAL DESCRIPTION

The plant descriptions and measurements were taken indoors in Gilroy, Calif. in April 2019. The plants were approximately 8 months old and were growing in 1 gallon pots in a greenhouse.

The aforementioned photographs show those same plants as used for the description were taken in Gilroy, Calif. in April 2019 and show 8 month old plants from an indoor trial.

Color references are made to The Royal Horticultural Society Colour Chart (RHS) 2001.

TABLE 1

DIFFERENCES BETWEEN THE NEW VARIETY 'LANZ0019' AND A MOST SIMILAR VARIETY

| | 'LANZ0019' | 'LANZ0007', U.S. Plant Pat. No. 28,174 |
|---|---|---|
| Flower color and size: | Dark orange mature flowers; medium-large sized | Golden yellow to orange flowers with an orange throat; large sized |
| Plant width: | 65 cm | 36-42 cm |
| Foliage: | Medium green | Dark green |

Plant:

*Form, growth and habit.*—Semi-woody, grown as an annual or perennial; dense mounding habit; very well branched.

*Plant height.*—24 cm.

*Plant height* (*inflorescence included*).—25 cm.

*Plant width.*—65 cm.

Foliage:

*Type.*—Opposite.

*Fragrance.*—Strongly scented.

*Immature, leaf color, upper surface.*—RHS 137B.

*Lower surface.*—RHS 138A.

*Mature, leaf color, upper surface.*—RHS 139A.

*Lower surface.*—RHS 137C.

*Length.*—7.5-8.2 cm.

*Width.*—5.2-5.6 cm.

*Shape.*—Ovate.

*Base shape.*—Rounded.

*Apex shape.*—Mucronate.

*Margin.*—Serrate.

*Texture, upper surface.*—Strigose.

*Texture, lower surface.*—Strigose.

*Pattern of veining.*—Pinnate.

*Petioles color.*—RHS 139B.

*Petioles length.*—1.4-2.0 cm.

*Diameter of petiole.*—0.20 cm.

*Texture* (*upper and lower surface*).—Very short hairs.

Stem:

*Color of stem.*—RHS 137C.

*Length of stem.*—19-24 cm.

*Diameter.*—0.2-0.3 cm.

*Length of internodes.*—2.5-4.1 cm.

*Texture.*—Hirsute.

Inflorescence:

*Type.*—Umbel like, flattened semi-sphere the florets are sessile on an ovate receptacle.

*Blooming habit.*—Flowers continuously from spring through fall.

*Number of open flowers per inflorescence.*—About 32-34.

*Quantity of inflorescences per plant.*—About 25-33.

*Lastingness of individual blooms on the plant.*—About 3 weeks (depending on temperatures).

*Fragrance.*—Slightly spicy.

*Umbel horizontal diameter.*—4.5-4.8 cm.

*Umbel vertical height.*—2.0-2.4 cm.

*Peduncle color.*—RHS 138B.

*Length of peduncle.*—4.4-5.0 cm.

*Peduncle diameter.*—0.15 cm.

*Texture.*—Scabrous.

Flower:

*Floret form.*—Corolla salver-shaped to shallow cup-shaped, with a relatively long tube at the base; each flower subtended by a single bract.

*Length of floret.*—2.1 cm.

*Width of floret.*—1.3-1.5 cm.

*Depth of floret.*—1.4 cm.

*Young floret, color upper surface.*—RHS 9A.

*Young floret, color lower surface.*—RHS 5A.

*Mid age floret, color upper surface.*—RHS 26A and RHS 9A.

*Mid age floret, color lower surface.*—RHS 168C and RHS 13B.

*Mature florets, color upper surface.*—RHS 45A and RHS 24A.

*Mature floret, color lower surface.*—RHS 168C and RHS 13B.

*Apex shape.*—Rounded.

*Degree of lobation.*—Moderate.

*Margin.*—Entire.

*Base.*—Fused.

*Texture, upper surface.*—Smooth.

*Lower surface.*—Smooth.

*Tube, color outer surface.*—Closest to RHS 163D and RHS 179C.

*Tube, color inner surface.*—Closest to RHS 168D.

*Tube, length.*—1.1-1.2 cm.

*Tube, diameter* (*at opening*).—0.2 cm.

*Tube, texture outer surface.*—Smooth.

*Inner surface.*—Smooth.

Bud (just before opening):

*Color.*—RHS 20B.

*Length.*—0.7-0.9 cm.

*Width.*—0.35 cm at the apex.

*Shape.*—Tubular with a flared apex.

Bract:

*Color.*—Closest to RHS 139A.

*Length.*—0.9-1.0 cm.

*Diameter.*—0.25 cm.

*Texture, upper surface.*—Small hairs.

*Lower surface.*—Small hairs.

Calyx:

*Number of sepals.*—5, fused sepals forming a short tube around the base of the floret.

*Color of sepals.*—RHS 144A.

*Length of sepals.*—0.3-0.4 cm.

*Width of sepals.*—0.1 cm.

*Apex shape.*—Obtuse.

*Apex Margins.*—Entire.

*Texture, outer surface.*—Small hairs.

*Inner surface.*—Smooth.

Reproductive organs:

*Gynoecium.*

*Pistil quantity.*—One.

*Length.*—0.35 cm.

*Style color.*—RHS 159D.

*Style length.*—0.2 cm.

*Stigma color.*—RHS 144D.

*Ovary color.*—RHS 144B.

*Ovary length.*—0.1 cm.

*Ovary diameter.*—0.05 cm.

*Androecium.*

*Stamen quantity.*—4.

*Color of filaments.*—RHS 159D.

*Length filaments.*—0.05 cm.

*Anther color.*—RHS 166A.

*Length of anthers.*—0.1 cm.

*Color of pollen.*—RHS 2D.

*Pollen amount.*—Scant.

*Fertility/seed set.*—Moderate.

*Fruit.*—Round drupe.

*Immature fruit color.*—RHS 146B.

*Mature fruit color.*—RHS 202A.

*Mature fruit size.*—0.6-0.8 cm in diameter.

*Texture of mature fruit.*—Fleshy.

*Disease/pest resistance.*—Has not been observed to date.

*Plant hardiness zone.*—Hardy to zone 9B.

*Heat/cold tolerant.*—Very heat tolerant.

What is claimed is:

1. A new and distinct variety of *Lantana* plant named 'LANZ0019' substantially as illustrated and described herein.

* * * * *